United States Patent [19]

Schroeder et al.

[11] Patent Number: 5,478,940
[45] Date of Patent: Dec. 26, 1995

[54] DOUBLE BENZIMIDAZOLES

[75] Inventors: Gunter-Rudolf Schroeder, Heidelberg; Udo Mayer, Frankenthal; Karin H. Beck, Ludwigshafen; Rainer Dyllick-Brenzinger, Weinheim, all of Germany

[73] Assignee: BASF Aktiengesellschaft, Ludwigshafen, Germany

[21] Appl. No.: 343,957

[22] Filed: Nov. 17, 1994

[30] Foreign Application Priority Data

Nov. 24, 1993 [DE] Germany ............... 43 39 959.2

[51] Int. Cl.⁶ ............ C07D 471/04; C07D 487/04
[52] U.S. Cl. ............ 544/370; 546/85; 548/302.4
[58] Field of Search ............ 548/302.4; 546/85; 544/370

[56] References Cited

U.S. PATENT DOCUMENTS

| | | |
|---|---|---|
| 4,212,644 | 7/1980 | Degen et al. . |
| 4,265,990 | 5/1981 | Stolka et al. . |
| 4,912,006 | 3/1990 | Breitschaft et al. . |

FOREIGN PATENT DOCUMENTS

| | | |
|---|---|---|
| 2106742 | 3/1994 | Canada . |
| 0590446A2 | 4/1994 | European Pat. Off. . |
| 2733468 | 2/1979 | Germany . |

*Primary Examiner*—Robert W. Ramsner
*Assistant Examiner*—Laura L. Stockton
*Attorney, Agent, or Firm*—Oblon, Spivak, McClelland, Maier & Neustadt

[57] ABSTRACT

Benzimidazoles of the formula

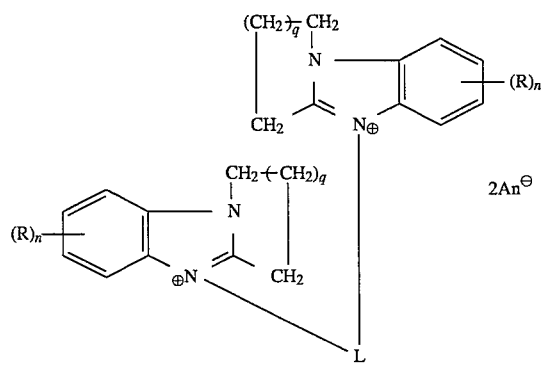

where $n$ and $q$ are each 1 or 2, the radicals R are each hydrogen, chlorine or methyl, L is a bridge member and $An^{\ominus}$ is one equivalent of an anion, are used as charge stabilizers in electrostatic toners.

2 Claims, No Drawings

DOUBLE BENZIMIDAZOLES

The present invention relates to novel benzimidazoles of the formula I $$(I)$$

where
  n and q independently of one another are each 1 or 2,
  the radicals R independently of one another are each hydrogen, chlorine or methyl,
  L is a bridge member and
  An$^\ominus$ is one equivalent of an anion,
electrostatic toners containing the benzimidazoles as charge stabilizers and the use of the benzimidazoles as charge stabilizers.

DE-A-2,733,468 and US-A-4,912,006 disclose similar benzimidazole compounds. However, it has been found that they have poor performance characteristics when used as charge stabilizers in electrostatic toners.

Furthermore, specific phenylalkylbenzimidazoles are described in Prior European Patent Application EP-A-590,446.

It is an object of the present invention to provide novel benzimidazoles which have advantageous performance characteristics.

We have found that this object is achieved by the double benzimidazoles of the formula I which are defined at the outset.

All alkylene or alkenylene groups in the formula I may be either straight-chain or branched.

Suitable bridge members L are, for example, $C_2$–$C_{10}$-alkylene, $C_4$–$C_{10}$-alkenylene or a radical of the formula $$\text{CH}_2\text{—C}_6\text{H}_4\text{—CH}_2$$

or $$\text{CH}_2\text{CO—N(C}_4\text{H}_8\text{)N—COCH}_2$$

$C_2$–$C_{10}$-alkylene radicals are, for example, $(CH_2)_2$, $(CH_2)_3$, $(CH_2)_4$, $(CH_2)_5$, $(CH_2)_6$, $(CH_2)_7$, $(CH_2)_8$, $(CH_2)_9$, $(CH_2)_{10}$, $CH(CH_3)CH_2$ or $CH(CH_3)CH(CH_3)$.

$C_4$–$C_{10}$-alkenylene radicals are, for example, $CH_2CH=CHCH_2$, $CH_2CH=CH(CH_2)_2$ or $(CH_2)_2CH=CH(CH_2)_2$.

Preferred bridge members L are $C_2$–$C_8$-alkylene, $CH_2CH=CHCH_2$, $$\text{CH}_2\text{—C}_6\text{H}_4\text{—CH}_2$$

or $$\text{CH}_2\text{CO—N(C}_4\text{H}_8\text{)N—COCH}_2,$$

$C_2$–$C_8$-alkylene being particularly noteworthy.

Benzimidazoles of the formula I which have a symmetrical structure are preferred.

Suitable anions are, for example, inorganic or organic anions, for example halides, such as fluoride, chloride, bromide or iodide, hexafluorophosphate, tetrafluoroborate, formate, acetate, propionate, oxalate, benzenesulfonate, toluenesulfonate and tetraphenylborate.

Benzimidazoles of the formula I where
  q is 1,
  the radicals R are each hydrogen,
  L is $C_2$–$C_8$-alkylene and
  n and An$^\ominus$ each have the abovementioned meanings are particularly preferred.

Benzimidazoles of the formula I, where L is $C_2$–$C_5$-alkylene, are of particular interest.

The novel benzimidazoles of the formula I can be obtained by methods known per se, as described, for example, in DE-A-2,733,468.

Thus, a bridged benzimidazole of the formula II $$(II)$$

where n, q and R each have the abovementioned meanings, can be reacted with a compound of the formula III $$X—L—X \qquad (III)$$

where L has the abovementioned meanings and X is a leaving group, eg. chlorine, bromine or iodine, and, if required, the product can then be precipitated by means of a salt of the formula IV $$M^\oplus \ An^\ominus \qquad (IV)$$

where An$^\ominus$ has the abovementioned meanings and $M^\oplus$ is one equivalent of a metal cation, eg. sodium or potassium.

The novel benzimidazoles can advantageously be used as charge stabilizers in electrostatic toners.

Accordingly, the present invention furthermore relates to electrostatic toners containing a polymeric binder and, as a charge stabilizer, a benzimidazole of the formula I.

The amount of the benzimidazoles of the formula I in electrostatic toners is as a rule from 0.01 to 10% by weight, based on the weight of the toner.

The polymeric binders present in the novel electrostatic toners are known per se. They are as a rule thermoplastic and have a softening point of from 40° to 200° C., preferably from 50° to 130° C., in particular from 65° to 115° C. Examples of polymeric binders are polystyrene, copolymers of styrene with an acrylate or methacrylate, copolymers of styrene with butadiene and/or acrylonitrile, polyacrylates, polymethacrylates, copolymers of an acrylate or methacrylate with vinyl chloride or vinyl acetate, polyvinyl chloride, copolymers of vinyl chloride with vinylidene chloride, copolymers of vinyl chloride with vinyl acetate, polyester resins, epoxy resins, polyamides or polyurethanes.

In addition to the abovementioned benzimidazoles I and the polymeric binders, the novel toners may contain known amounts of colorants, magnetically attractable material, waxes and flow improvers.

The colorants may be organic dyes or pigments, such as nigrosine, aniline blue, 2,9-dimethylquinacridone, C.I. Disperse Red 15 (C.I. 6010), C.I. Solvent Red 19 (C.I. 26 050), C.I. Pigment Blue 15 (C.I. 74 160), C.I. Pigment Blue 22 (C.I. 69 810) or C.I. Solvent Yellow 16 (C.I. 12 700), or inorganic pigments, such as carbon black, red lead, yellow lead oxide or chrome yellow. In general, the amount of the colorant present in the toner does not exceed 15% by weight, based on the weight of the toner.

The magnetically attractable material may be, for example, iron, nickel, chromium oxide, iron oxide or a ferrite of the formula $MeFe_2O_4$, where Me is a divalent metal, eg. iron, cobalt, zinc, nickel or manganese.

The novel toners are prepared by conventional processes, for example by mixing the components in a kneader followed by pulverization, or by melting the polymeric binder or a mixture of the polymeric binders, then finely dispersing one or more benzimidazoles I and the other additives, if used, in the molten resin using the mixing and kneading apparatuses known for this purpose, then cooling the melt to give a solid mass and finally milling the solid mass to give particles having the desired particle size (as a rule from 0.1 to 50 µm). It is also possible to suspend the polymeric binder and the charge stabilizer in a common solvent and to add the other additives to the suspension. The suspension can thus be used as a fluid toner.

However, it is also possible to spray-dry the fluid in a manner known per se, to evaporate off the solvents or to freeze-dry the fluid and to mill the solid residue to give particles having the desired particle size.

Instead of dissolving the novel benzimidazoles used as charge stabilizers, it is also possible to disperse them finely in the solution of the polymeric binder. The toner composition thus obtained can then be used, for example according to US-A-4 265 990, in a xerographic image recording system.

The abovementioned benzimidazoles of the formula I are advantageous charge stabilizers. In particular, when added to a toner preparation, they impart an advantageous electrostatic charge profile to said preparation, ie. the toners can be charged rapidly and to a high level. The novel charge stabilizers also enable the charge to be kept constant at a high level.

The Examples which follow illustrate the invention.

A) Preparation of the benzimidazoles

Example H1

79.0 g (0.5 mol) of pyrrolidino[1,2-a]benzimidazole were dissolved in 90 ml of ethylene glycol monobutyl ether and the solution was heated to 120° C. 31.75 g (0.25 mol) of 1,4-dichlorobutane were added dropwise in the course of 1 hour. The temperature was then increased to 140° C. and stirring was continued for 2 hours. The mixture was cooled to 90° C., after which 300 ml of hot water were run in and stirring was continued for a further 2 hours. 60.4 g (0.55 mol) of sodium tetrafluoroborate were then added while stirring. The crystalline precipitate was filtered off with suction after 1 hour at 50° C. and was washed with water. The water-moist filter residue was dried under reduced pressure at 60° C. 86 g of a grayish white product of the formula

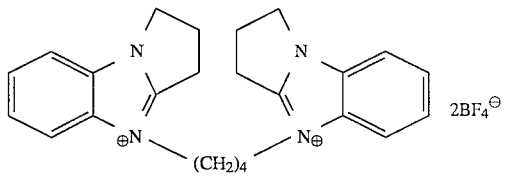

were obtained in this manner. The following benzimidazoles were obtained in a similar manner.

| Example No. | R | L | An$^\ominus$ |
|---|---|---|---|
| H 2 | H | $(CH_2)_2$ | $BF_4^\ominus$ |
| H 3 | H | $CH_2-CH=CH-CH_2$ | $BF_4^\ominus$ |
| H 4 | H | $(CH_2)_5$ | $BF_4^\ominus$ |
| H 5 | $CH_3$ | $(CH_2)_2$ | $BF_4^\ominus$ |
| H 6 | $CH_3$ | $(CH_2)_4$ | $BF_4^\ominus$ |
| H 7 | $CH_3$ | $CH_2-CH=CH-CH_2$ | $BF_4^\ominus$ |
| H 8 | $CH_3$ | $(CH_2)_5$ | $BF_4^\ominus$ |
| H 9 | H | $CH_2-\text{C}_6H_4-CH_2$ | $Cl^\ominus$ |
| H10 | $CH_3$ | $CH_2-\text{C}_6H_4-CH_2$ | $BF_4^\ominus$ |
| H11 | H | piperazine diacetyl linker | $BF_4^\ominus$ |

B) Use

The Use Examples were carried out using colorant-free toner models, consisting of resin and the novel charge stabilizers.

I. Preparation of the toners 0.2 g of benzimidazole was introduced into a solution of 10 g of a linear uncrosslinked polyester resin in 100 ml of xylene and the mixture was then freeze-dried. The resulting product was then milled (mean particle size 50 µm).

II. Preparation of the developers and testing

In the preparation of a developer, 99% by weight of a steel carrier which had a mean particle size of 100 µm and 1% by weight of the toner were accurately weighed and were activated on a roller stand over a period defined in detail below. The electrostatic charge of the developer was then determined. About 5 g of the activated developer were then introduced into a hard-blow-off cell, which was electrically connected to an electrometer, in a commercial q/m meter (Epping GmbH, Neufahrn). The mesh size of the sieve used in the measuring cell was 63 μm.

This ensured that the toner was blown off as completely as possible but the carrier remained in the measuring cell. By means of a strong airstream (about 4000 cm$^3$/min) and simultaneous suction, the toner was virtually completely removed from the carrier particles, the latter remaining in the measuring cell. The charge on the carrier was registered on the electrometer. It corresponded to the magnitude of the charge on the toner particles, but were the opposite sign. To calculate the q/m value, the magnitude of q was therefore used for the opposite sign. By reweighing the measuring cell, the mass of blown off toner was determined and the electrostatic charge q/m was calculated from this.

The charge determined for the toners is summarized in the Table below.

TABLE

| Example No. | Compound from Example | Charge after activation for [μC/g] | | | |
|---|---|---|---|---|---|
| | | 10 min | 30 min | 60 min | 120 min |
| A1 | H1 | 20.8 | 17.9 | 17.9 | 17.3 |
| A2 | H2 | 18.8 | 18.8 | 18.2 | 18.8 |
| A3 | H3 | 19.2 | 19.7 | 19.6 | 19.9 |
| A4 | H4 | 17.9 | 17.5 | 22.1 | 18.7 |
| A5 | H5 | 19.9 | 21.4 | 19.7 | 18.7 |
| A6 | H6 | 20.9 | 20.1 | 20.1 | 21.6 |
| A7 | H7 | 19.4 | 19.2 | 18.1 | 17.1 |
| A8 | H8 | 16.9 | 19.3 | 19.4 | 17.7 |
| A9 | H9 | | 13.1 | | |
| A10 | H10 | 15.2 | 14.7 | 15.5 | 14.8 |
| A11 | H11 | | 8.4 | | |

We claim:

1. A benzimidazole of the formula I

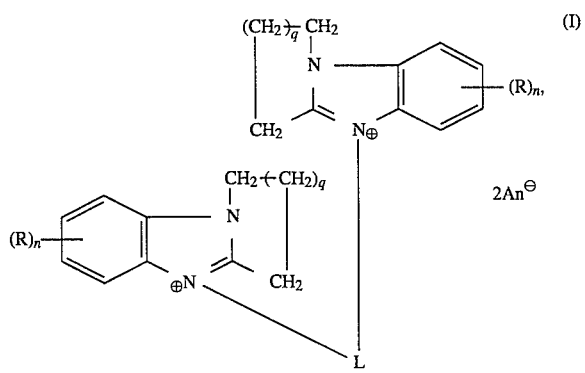

where n and q independently of one another are each 1 or 2, the radicals R independently of one another are each hydrogen, chlorine or methyl, L is a bridge member and $An^\ominus$ is one equivalent of an anion.

2. A benzimidazole as claimed in claim 1, wherein q is 1, the radicals R are each hydrogen and L is $C_2$–$C_8$-alkylene.

* * * * *